(12) United States Patent
Nair et al.

(10) Patent No.: US 8,829,254 B2
(45) Date of Patent: Sep. 9, 2014

(54) PROCESS FOR MAKING 1,3,3,3-TETRAFLUOROPROPENE

(71) Applicant: Honeywell International Inc., Morristown, NJ (US)

(72) Inventors: Haridasan K. Nair, Williamsville, NY (US); Rajiv Ratna Singh, Getzville, NY (US); David Nalewajek, West Seneca, NY (US); Andrew Joseph Poss, Kenmore, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/757,894

(22) Filed: Feb. 4, 2013

(65) Prior Publication Data

US 2013/0211155 A1 Aug. 15, 2013

Related U.S. Application Data

(60) Provisional application No. 61/598,531, filed on Feb. 14, 2012.

(51) Int. Cl.

| C07C 17/278 | (2006.01) |
|---|---|
| C07C 17/087 | (2006.01) |
| C07C 17/093 | (2006.01) |
| C07C 17/20 | (2006.01) |
| C07C 17/23 | (2006.01) |
| C07C 17/25 | (2006.01) |
| C07C 19/01 | (2006.01) |
| C07C 19/10 | (2006.01) |
| C07C 21/04 | (2006.01) |
| C07C 21/18 | (2006.01) |

(52) U.S. Cl.
CPC .............. *C07C 17/25* (2013.01); *C07C 17/278* (2013.01); *C07C 17/206* (2013.01); *C07C 17/23* (2013.01)
USPC ........... 570/155; 570/156; 570/157; 570/158; 570/164; 570/220; 570/237

(58) Field of Classification Search
CPC ...................................................... C07C 17/25
USPC .......... 570/155, 156, 157, 158, 237, 220, 164
See application file for complete search history.

(56) References Cited

U.S. PATENT DOCUMENTS

| 5,026,460 | A | * | 6/1991 | Dapperheld | .................. 205/338 |
|---|---|---|---|---|---|
| 5,811,603 | A | | 9/1998 | Elsheikh | |
| 5,969,198 | A | * | 10/1999 | Thenappan et al. | .......... 570/167 |
| 5,986,151 | A | | 11/1999 | Van Der Puy | |
| 6,124,510 | A | | 9/2000 | Elsheikh et al. | |
| 6,548,719 | B1 | | 4/2003 | Nair et al. | |
| 6,596,910 | B2 | * | 7/2003 | Tung et al. | .................... 570/167 |
| 7,829,748 | B1 | | 11/2010 | Tung et al. | |
| 2007/0129580 | A1 | * | 6/2007 | Mukhopadhyay et al. | ... 570/155 |
| 2009/0043137 | A1 | * | 2/2009 | Wang et al. | .................... 570/136 |

FOREIGN PATENT DOCUMENTS

| WO | 2005-108332 | | 11/2005 |
|---|---|---|---|
| WO | 2010059493 | A1 | 5/2010 |
| WO | 2011-034991 | | 3/2011 |

OTHER PUBLICATIONS

Kotora, M. et al. Journal of Molecular Catalysis 1992, 77, 51-60.*
Sridhar, M. et al. Tetrahedron 2000, 56, 3539-3545.*
PCT Search Report & Written Opinion from PCT/US2013/024835 dated May 3, 2013.

* cited by examiner

*Primary Examiner* — Jafar Parsa
*Assistant Examiner* — Medhanit Bahta
(74) *Attorney, Agent, or Firm* — Erika S. Wilson

(57) ABSTRACT

The present invention describes a process for making $CF_3CH=CHF$ (HFO-1234ze). The process involves the addition of carbon tetrachloride ($CCl_4$) to 1,2-dichloroethylene to form $CCl_3CHClCHCl_2$. The compound $CCl_3CHClCHCl_2$ thus can then either be treated with HF to produce $CF_3CHClCHClF$ as the main product, or it can be converted to $CCl_2=CHCHCl_2$ (1230za) by dechlorination. $CCl_2=CHCHCl_2$ can be treated with HF such that the main product obtained is $CF_3CHClCHClF$. $CF_3CH=CHCl$ may be produced as a by-product, but upon treatment with HF, it affords the compound $CF_3CHClCHClF$. The desired compound, $CF_3CH=CHF$ (HFO-1234ze), is obtained as a trans/cis mixture by dehydrochlorination of $CF_3CH_2CHClF$ or by dechlorination of $CF_3CHClCHClF$.

35 Claims, No Drawings

PROCESS FOR MAKING 1,3,3,3-TETRAFLUOROPROPENE

CROSS-REFERENCE TO RELATED APPLICATION

This application claims domestic priority under 35 U.S.C. 119(e) to commonly owned U.S. Provisional Application Ser. No. 61/598,531, filed 14 Feb. 2012, the disclosure of which is hereby incorporated herein by reference.

FIELD OF THE INVENTION

The present invention describes a process for making a tetrafluorinated propene compound. More specifically, the invention describes a process for making the compound 1,3,3,3-tetrafluoropropene ($CF_3CH=CHF$, HFO-1234ze or 1234ze).

BACKGROUND OF THE INVENTION

The tetrafluoropropene compound HFO-1234ze, is a useful compound with low global warming potential. HFO-1234ze is useful in numerous applications including as a foam blowing agent, refrigerant, and as monomer for homopolymers and copolymers.

Several methods are known for the preparation of HFO-1234ze. For example, U.S. Pat. No. 6,548,719 describes the production of many fluoro-olefins including $CF_3CH=CHF$ from $CF_3CH_2CF_2H$ (245fa) by dehydrohalogenation in the presence of a phase transfer catalyst. U.S. Pat. Nos. 5,986,151 and 6,124,510 describe the gas phase catalytic dehydrofluorination of $CF_3CH_2CF_2H$ to afford $CF_3CH=CHF$. These documents are hereby incorporated herein by reference.

Gas phase dehydrochlorination of $CF_3CH_2CHFCl$ (244fa) is reported to give $CF_3CH=CHF$ as described in U.S. Pat. No. 7,829,748. Vapor phase fluorination of $CF_3CH=CHCl$ (1233zd) with HF and $SbF_5$ catalyst affords HFO-1234ze along with 245fa and $CHClF-CF_2-CF_3$. See, for example, U.S. Pat. No. 7,829,748. This document is hereby incorporated herein by reference.

The main disadvantages of the above described methods are that in each case the starting materials, for example $CF_3CH_2CF_2H$, typically need to be made by multiple reaction steps, and/or with relatively expensive raw materials, and thus there is a need to provide an improved process for the production of HFO-1234ze, at least from a cost effectiveness viewpoint.

Accordingly, the present invention has been developed, namely a process which utilizes relatively inexpensive and commercially available starting materials for making HFO-1234ze as detailed below.

SUMMARY OF THE INVENTION

The present invention is directed to a process for making $CF_3CH=CHF$ (HFO-1234ze). The process involves the addition of carbon tetrachloride to 1,2-dichloro-ethylene to form $CCl_3CHClCHCl_2$. The compound $CCl_3CHClCHCl_2$ can then either be treated with HF to produce $CF_3CHClCHClF$ as the main product, or it can be converted to $CCl_2=CHCHCl_2$ (HCC-1230za) by dechlorination. $CCl_2=CHCHCl_2$ can be treated with HF such that the main product obtained is $CF_3CHClCHClF$.

$CF_3CH=CHCl$ may be produced as a by-product, but upon treatment with HF, it affords $CF_3CHClCHClF$. The desired compound, $CF_3CH=CHF$ (HFO-1234ze), is obtained as a trans/cis mixture by dehydrochlorination of $CF_3CH_2CHClF$ or by dechlorination of $CF_3CHClCHClF$, respectively. These reactions are shown in the following schemes:

Scheme 1

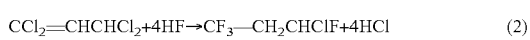

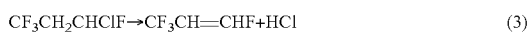

Scheme 2

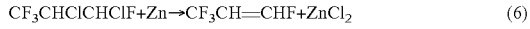

DETAILED DESCRIPTION OF THE INVENTION

As described above, the process involves the addition of carbon tetrachloride ($CCl_4$) to 1,2-dichloroethylene (trans, cis or a mixture) to form $CCl_3CHClCHCl_2$. The compound $CCl_3CHClCHCl_2$ can be either be fluorinated with HF such that the main product obtained is $CF_3CHClCHClF$, or it can be converted to $CCl_2=CHCHCl_2$ (1230za) by dechlorination. $CCl_2=CHCHCl_2$ can be fluorinated with HF such that the main product obtained is $CF_3CHClCHClF$. $CF_3CH=CHCl$ may be produced as a by-product, but upon treatment with HF, it affords $CF_3CHClCHClF$. The desired compound, $CF_3CH=CHF$ (HFO-1234ze), is obtained as a trans/cis mixture by dehydrochlorination of $CF_3CH_2CHClF$ or by dechlorination of $CF_3CHClCHClF$.

Addition of $CCl_4$ to $CHCl=CHCl$ (trans, cis or mixture) can be conducted with a catalyst comprising, for example, a copper or ruthenium complex catalyst at about 80° C. to afford mainly $CCl_3CHClCHCl_2$, as described in J. Molecular Catalysis, 77, (1992) 51-60. Chlorotris(triphenylphosphine) rhodium can also be used as a catalyst instead of $RuCl_2(PPh_3)_3$. Additionally, commercially available immobilized catalyst such as polymer bound $RuCl(PPh_3)_3$ also effects this addition.

The compound $CCl_3CHClCHCl_2$ is converted to $CCl_2=CHCHCl_2$ (1230za) via dechlorination with Zn. The reaction conditions can be optimized to afford $CCl_2=CHCHCl_2$ in good yield. It should be noted that $CCl_2=CHCHCl_2$ can also be obtained by pyrolysis of tetrachlorocyclopropane (see J. Chem. Soc. Section C (Organic), 1969, 165-172) or from polyhaloacrolein reacted with HCl and aluminum halides as described in Bulletin de la Societe Chimique de France 1963, 10, 2147-53.

The compound 1230za ($CCl_2=CHCHCl_2$) is fluorinated with HF (see U.S. Pat. No. 5,811,603 and PCT Publication No. WO 2010/059493A1) to afford $CF_3CH_2CHClF$ (244fa) or $CF_3CH=CHCl$ (1233zd); the latter is readily converted to $CF_3CH_2CHClF$ (see U.S. Patent Pub. No. 2011-0201853). Fluorination reactions are typically carried out with hydrogen fluoride, preferably anhydrous HF (AHF) and a fluorination catalyst. These catalysts are well known, and one can fine tune the reaction conditions to afford mainly the desired product $CF_3CH_2CHClF$. These documents are hereby incorporated herein by reference.

In the last step, dehydrochlorination of $CF_3CH_2CHClF$ affords $CF_3CH=HF$ (HFO-1234ze). Alternately, any $CCl_3CHClCHCl_2$ formed can be fluorinated with HF to afford $CF_3CHClCHClF$ which can then be dechlorinated with zinc to afford HFO-1234ze.

Example 1

Addition of $CCl_4$ to $CHCl=CHCl$

Into a clean, dry 1 L autoclave was added $CHCl=CHCl$ (trans and/or cis) (24.0 g, 0.250 mol), carbon tetrachloride (400 mL) and $RuCCl_2(PPh_3)_3$ (2.3 g, 2.5 mmol) under nitrogen purge. The sealed autoclave was then heated to and maintained at 80° C. for about 8 hours. The reaction mixture was filtered through silica gel pad and analyzed by GC which indicated greater than 80% conversion. The product $CCl_3CHClCHCl_2$ was isolated by distillation, and the yield ranged from 40% to 50% over three runs.

Example 1a

This reaction was conducted in the same manner as Example 1, except for the fact that chlorotris(triphenylphosphine)rhodium, $RhCl(PPh_3)_3$, was used instead of $RuCl_2(PPh_3)_3$. The yield ranged from 35-55%.

Note that the reaction can also be conducted using an immobilized catalyst, for example, polymer bound $RuCl(PPh_3)_3$ which is commercially available.

Example 2

Conversion of $CCl_3CHClCHCl_2$ to $CCl_2=CHCHCl_2$

To a heated (50° C. to 60° C.) mixture of zinc dust (25 mmol) and methanol (50 mL) was added $CCl_3CHClCHCl_2$ (50 mmol) drop-wise. The product, $CCl_2=CHCHCl_2$, formed was collected in a cold trap to afford 60% to 70% yield; the remaining product was $CCl_3CH=CHCl$. The latter can be converted to $CF_3CH_2CHClF$ with HF.

Example 3

Reaction of $CCl_3CHClCHCl_2$ with HF

The fluorination reaction was conducted in a Monel® tube reactor (2.54 cm diameter, 80 cm long). The reactor was charged with 150 g fluorination catalyst $SbCl_5$ (or $SbF_5$, or $SbCl_xF_y$, where x+y=5) on activated carbon (Togo Colon PCB, 4×10 mesh) and heated to 85° C. as described in U.S. Pat. No. 7,829,748. Then, a mixture of vaporized $CCl_3CHClCHCl_2$ and anhydrous HF (about 1:10) was passed through the heated catalyst with a contact time of between 2 sec. to 10 sec. Contact time=bulk volume of catalyst/volumetric flow rate of reactants in ml/sec.

The flow rate of each reactant was controlled with a mass flow meter/controller in such a way that the contact time was in the range of 2 sec. to 10 sec. The effluent mainly consisted of $CF_3CHClCHClF$. For example, with a contact time of 2 sec., at 60° C. to 70° C., the yield of $CF_3CHClCHClF$ ranged from 30% to 40% as determined by GC area; the remainder being by-products, $CF_3CHClCHF_2$ and $CF_3CHFCHF_2$; $CF_3CHClCHClF$ was separated by distilling (bp=71° C.).

Example 4

Reaction of HF with $CCl_2=CHCHCl_2$

Fluorination of $CCl_2=CHCHCl_2$ was conducted as in Example 3. The main product obtained was $CF_3CH_2CHClF$ along with $CF_3CH=CHCl$ (20% to 30%); the latter product formed can be converted to the former with more HF.

Example 5

Conversion of $CF_3CHClCHClF$ to $CF_3CH=CFH$

Dechlorination of $CF_3CHClCHClF$ was accomplished as described in Example 2. Thus, 65% yield of HFO-1234ze ($CF_3CH=CHF$) was obtained when 0.2 mol of $CF_3CHClCHClF$ was dechlorinated with Zn (0.11 mol) dust in methanol (50 mL) at 50° C. to 60° C.

Example 6

Dehydrochlorination of $CF_3CH_2CHClF$

Liquid Phase

Into a 0.5 L Teflon lined autoclave was charged 300 g of 20% aq. KOH solution, 1 g Aliquat 336 or 18-crown ether and 20 g $CF_3CH_2CHClF$. The contents in the autoclave were heated to and maintained at 50° C. to 55° C. for 6 hours. The progress of the reaction was monitored by GC. After 12 hours, the product HFO-1234ze (65% yield) was collected in a steel cylinder cooled at −78° C.

Vapor Phase

In a Monel tube reactor, 20 cc of acid treated (HCl or $HNO_3$) activated carbon catalyst was loaded and heated to 350° C. to 370° C. Then vapor stream of $CF_3CH_2CHClF$ at a rate about 6 g/h was passed through the heated catalyst bed in the reactor for from 1 hour to 8 hours. The conversion of 244fa ranged from 40% to 60% with a selectivity of HFO-1234ze greater than 95%. Further purification was accomplished by distillation.

Continuous Operation

Each of the reactions described above can be operated in either a batch mode or in a continuous mode. In a continuous operation mode the various reaction starting materials are continuously fed into the reactor at desired ratio. Catalyst and/or any other desired reaction additives can be added into reactor periodically or continuously, but the continuous mode is preferred. The reactions are preferably carried out at a residence time of from about 0.01 hours to about 24 hours, preferably from about 1 hour to about 12 hours. The reaction conditions are judicially selected for high reaction efficiency.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making $CF_3CH=CHF$ comprising the steps of:
   (a) converting 1,2-dichloroethylene to the compound $CCl_3CHClCHCl_2$ by an addition reaction with $CCl_4$;
   (b) converting $CCl_3CHClCHCl_2$ to the compound $CCl_2=CHCHCl_2$ by a dechlorination reaction;
   (c) fluorinating the product of step (b) to form the compound $CF_3CH_2CHClF$; and
   (d) dehydrochlorinating the product of step (c) to form the compound $CF_3CH=CHF$.

2. The process of claim 1, wherein the reaction of step (a) is conducted with a catalyst.

3. The process of claim 2, wherein the catalyst comprises a copper catalyst.

4. The process of claim 2, wherein the catalyst comprises a ruthenium catalyst.

5. The process of claim 1, wherein the dechlorination reaction of step (b) is conducted using zinc.

6. The process of claim 1, wherein the fluorination reaction of step (c) is conducted with hydrogen fluoride and a fluorination catalyst.

7. The process of claim 6, wherein the hydrogen fluoride is anhydrous.

8. The process of claim 6, wherein the fluorination catalyst has the formula $SbCl_xF_y$, where x+y=5.

9. The process of claim 6, wherein the fluorination catalyst comprises $SbCl_5$.

10. The process of claim 6, wherein the fluorination catalyst comprises $SbF_5$.

11. The process of claim 6, wherein the fluorination catalyst is supported on activated carbon.

12. The process of claim 1, wherein the dehydrochlorination reaction of step (d) is conducted in either the liquid phase or the gas phase, with a dehydrochlorination catalyst.

13. The process of claim 12, wherein the dehydrochlorination reaction is conducted in the liquid phase.

14. The process of claim 13, wherein the catalyst comprises an alkali metal hydroxide with a phase transfer catalyst.

15. The process of claim 14, wherein the alkali metal hydroxide comprises sodium hydroxide.

16. The process of claim 14, wherein the alkali metal hydroxide comprises potassium hydroxide.

17. The process of claim 12, wherein the dehydrochlorination reaction is conducted in the gas phase.

18. The process of claim 17, wherein the catalyst comprises acid treated activated carbon.

19. The process of claim 18, wherein the acid treatment is selected from HCl and $HNO_3$.

20. The process of claim 17, wherein the dehydrochlorination reaction is conducted at a temperature range of from about 300° C. to 500° C.

21. The process of claim 17, wherein the dehydrochlorination reaction is conducted at a temperature range of from about 350° C. to 370° C.

22. A process for making $CF_3CH=CHF$ comprising the steps of:
   (a) reacting carbon tetrachloride with 1,2-dichloroethylene to form the compound $CCl_3CHClCHCl_2$;
   (b) fluorinating the compound $CCl_3CHClCHCl_2$ with HF to produce the compound $CF_3CHClCHClF$; and
   (c) dechlorinating $CF_3CHClCHClF$ to produce the compound $CF_3CH=CHF$.

23. The process of claim 22, wherein the dechlorination reaction is conducted with zinc.

24. The process of claim 22, wherein a portion of the compound $CCl_3CHClCHCl_2$ is converted to the compound $CCl_2=CHCHCl_2$ (HCC-1230za) by a dechlorination reaction.

25. The process of claim 22, wherein a portion of the compound $CCl_3CHClCHCl_2$ is fluorinated with HF and a fluorination catalyst to afford the compound $CF_3CHClCHClF$.

26. The process of claim 25, wherein the fluorination catalyst has the formula $SbCl_xF_y$, where x+y=5.

27. The process of claim 26, wherein the fluorination catalyst comprises $SbCl_5$.

28. The process of claim 26, wherein the fluorination catalyst comprises $SbF_5$.

29. The process of claim 26, wherein the fluorination catalyst is supported on activated carbon.

30. The process of claim 24, further comprising the step wherein the compound $CCl_2=CHCHCl_2$ is fluorinated with HF and a fluorination catalyst to produce the compound $CF_3CHClCHClF$.

31. The process of claim 30, further comprising the step wherein the dechlorination of $CF_3CHClCHClF$ affords the compound $CF_3CH=HF$ (HFO-1234ze).

32. The process of claim 22, wherein the dechlorination reaction also produces the compound $CF_3CH=CHCl$ as a by-product.

33. The process of claim 32, further comprising the step wherein the by-product compound $CF_3CH=CHCl$ is fluorinated with hydrogen fluoride and a fluorination catalyst to produce the compound $CF_3CHClCHClF$.

34. The process of claim 1, wherein the reactions are conducted in a continuous manner.

35. The process of claim 22, wherein the reactions are conducted in a continuous manner.

* * * * *